United States Patent
Ludin et al.

(10) Patent No.: US 9,907,936 B2
(45) Date of Patent: Mar. 6, 2018

(54) DETECTION AND CLEARING OF OCCLUSIONS IN CATHETERS

(71) Applicant: INTEGRA LIFESCIENCES SWITZERLAND SÀRL, Le Locle (CH)

(72) Inventors: Lev Ludin, Newton, MA (US); Michael Defusco, North Attleboro, MA (US)

(73) Assignee: INTEGRA LIFESCIENCE SWITZERLAND SÀRL, Le Locle (CH)

( * ) Notice: Subject to any disclaimer, the term of this patent is extended or adjusted under 35 U.S.C. 154(b) by 0 days.

(21) Appl. No.: 14/803,238

(22) Filed: Jul. 20, 2015

(65) Prior Publication Data

US 2016/0184562 A1    Jun. 30, 2016

Related U.S. Application Data

(62) Division of application No. 13/828,084, filed on Mar. 14, 2013, now Pat. No. 9,084,620.

(51) Int. Cl.
*A61M 27/00*   (2006.01)
*A61B 18/14*   (2006.01)
(Continued)

(52) U.S. Cl.
CPC ....... *A61M 27/006* (2013.01); *A61B 18/1492* (2013.01); *A61B 18/18* (2013.01);
(Continued)

(58) Field of Classification Search
CPC .......... A61B 18/18; A61M 2025/0019; A61M 2025/0166; A61M 2202/0464;
(Continued)

(56) References Cited

U.S. PATENT DOCUMENTS

| 4,411,648 | A | * | 10/1983 | Davis | A61N 1/306 604/21 |
| 5,324,275 | A | * | 6/1994 | Raad | A61N 1/40 604/20 |

(Continued)

FOREIGN PATENT DOCUMENTS

| EP | 1491231 A1 | 12/2004 |
| EP | 1614442 A2 | 1/2006 |

(Continued)

OTHER PUBLICATIONS

Columbian Office Action dated Mar. 8, 2016, issued to corresponding Application No. 14-53006-4.

*Primary Examiner* — Adam Marcetich
(74) *Attorney, Agent, or Firm* — Troutman Sanders LLP

(57) ABSTRACT

A catheter system with integral sensing and clearing of occlusions is described. The system can include a catheter in fluid communication with a shunt for transporting a bodily fluid within, or out of, a patient's body. The catheter and/or the shunt can include one or more detection wires and one or more transmission wires. The detection wires can be in electrical communication with the fluid and can enable the detection of changes in electrical properties of the fluid indicating an occlusion, or other anomaly, in the catheter. The transmission wires can be in electrical communication with the fluid and can enable the application of electromagnetic energy to the occlusion to facilitate its removal. The detection wires and the transmission wires can be the same or different wires. The system can include a probe that can be externally connected to the wires to provide detection and or transmission signals.

11 Claims, 14 Drawing Sheets

(51) Int. Cl.
*A61B 18/18* (2006.01)
*A61M 5/168* (2006.01)
*A61M 25/00* (2006.01)
*A61M 25/01* (2006.01)

(52) U.S. Cl.
CPC ...... *A61M 5/16831* (2013.01); *A61M 25/007* (2013.01); *A61M 25/0067* (2013.01); *A61M 25/0074* (2013.01); *A61M 25/0082* (2013.01); *A61M 27/002* (2013.01); *A61M 25/005* (2013.01); *A61M 2025/0019* (2013.01); *A61M 2025/0166* (2013.01); *A61M 2202/0464* (2013.01); *A61M 2205/33* (2013.01); *A61M 2205/3303* (2013.01); *A61M 2205/3317* (2013.01); *A61M 2210/0687* (2013.01); *A61M 2210/0693* (2013.01)

(58) Field of Classification Search
CPC ...... A61M 2205/33; A61M 2205/3303; A61M 2205/3317; A61M 2210/0687; A61M 2210/0693

See application file for complete search history.

(56) References Cited

U.S. PATENT DOCUMENTS

| | | | | |
|---|---|---|---|---|
| 5,328,451 | A * | 7/1994 | Davis | A61N 1/306 422/22 |
| 6,119,037 | A * | 9/2000 | Kellogg | A61N 1/044 604/21 |
| 6,248,080 | B1 | 6/2001 | Misel et al. | |
| 2003/0158584 | A1* | 8/2003 | Cates | A61B 5/0031 607/2 |
| 2004/0267186 | A1* | 12/2004 | Dextradeur | A61M 25/0068 604/8 |
| 2006/0235349 | A1 | 10/2006 | Osborn et al. | |
| 2006/0254600 | A1* | 11/2006 | Danek | A61B 1/00085 128/898 |
| 2008/0039770 | A1 | 2/2008 | Francis et al. | |
| 2009/0048648 | A1* | 2/2009 | Dacey, Jr. | A61F 2/30 607/88 |
| 2010/0233021 | A1* | 9/2010 | Sliwa | A61M 25/0017 422/20 |
| 2010/0256616 | A1* | 10/2010 | Katoh | A61B 18/1492 606/7 |
| 2013/0165917 | A1* | 6/2013 | Mathur | A61B 18/18 606/33 |

FOREIGN PATENT DOCUMENTS

| | | |
|---|---|---|
| WO | 2007092618 A2 | 8/2007 |
| WO | 2011158244 A2 | 12/2011 |

* cited by examiner

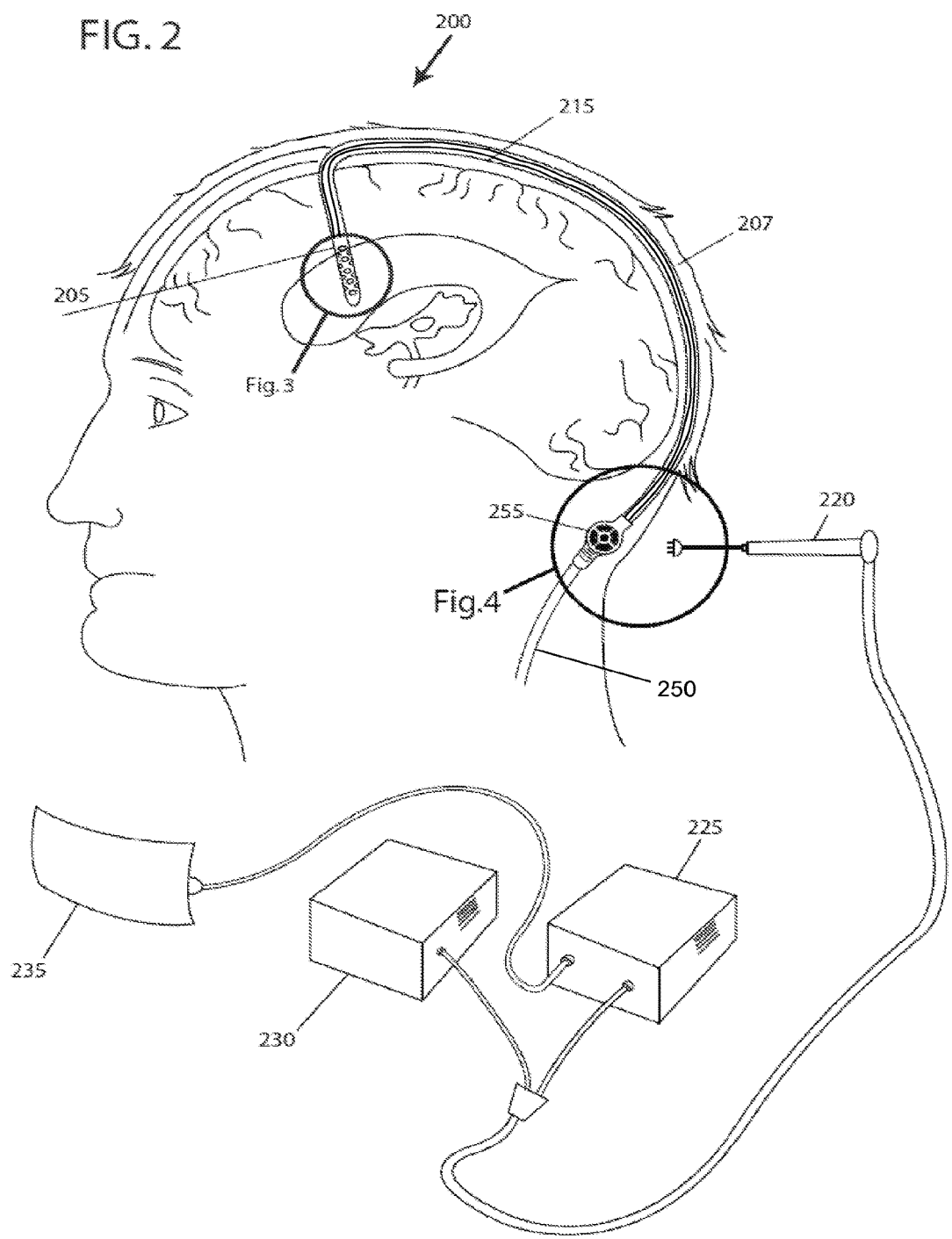

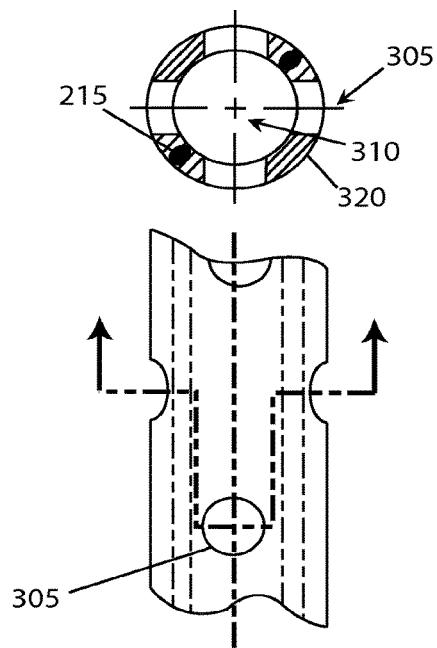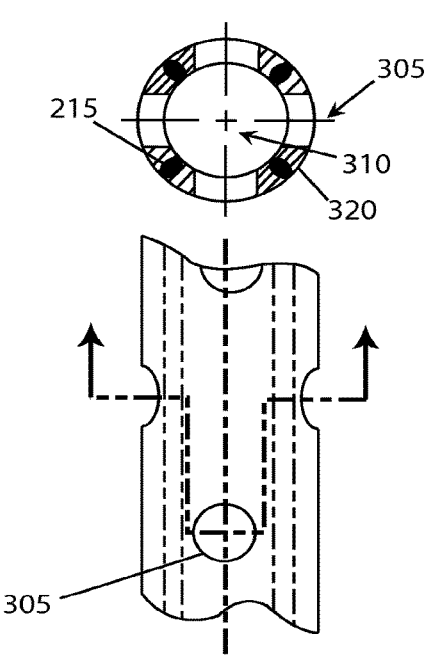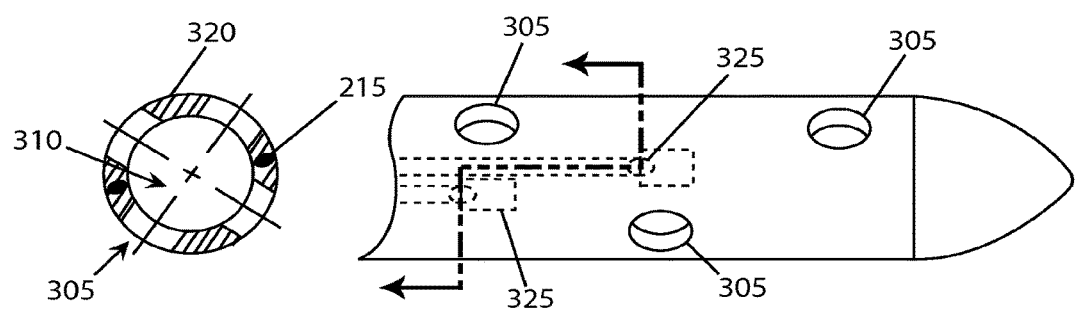

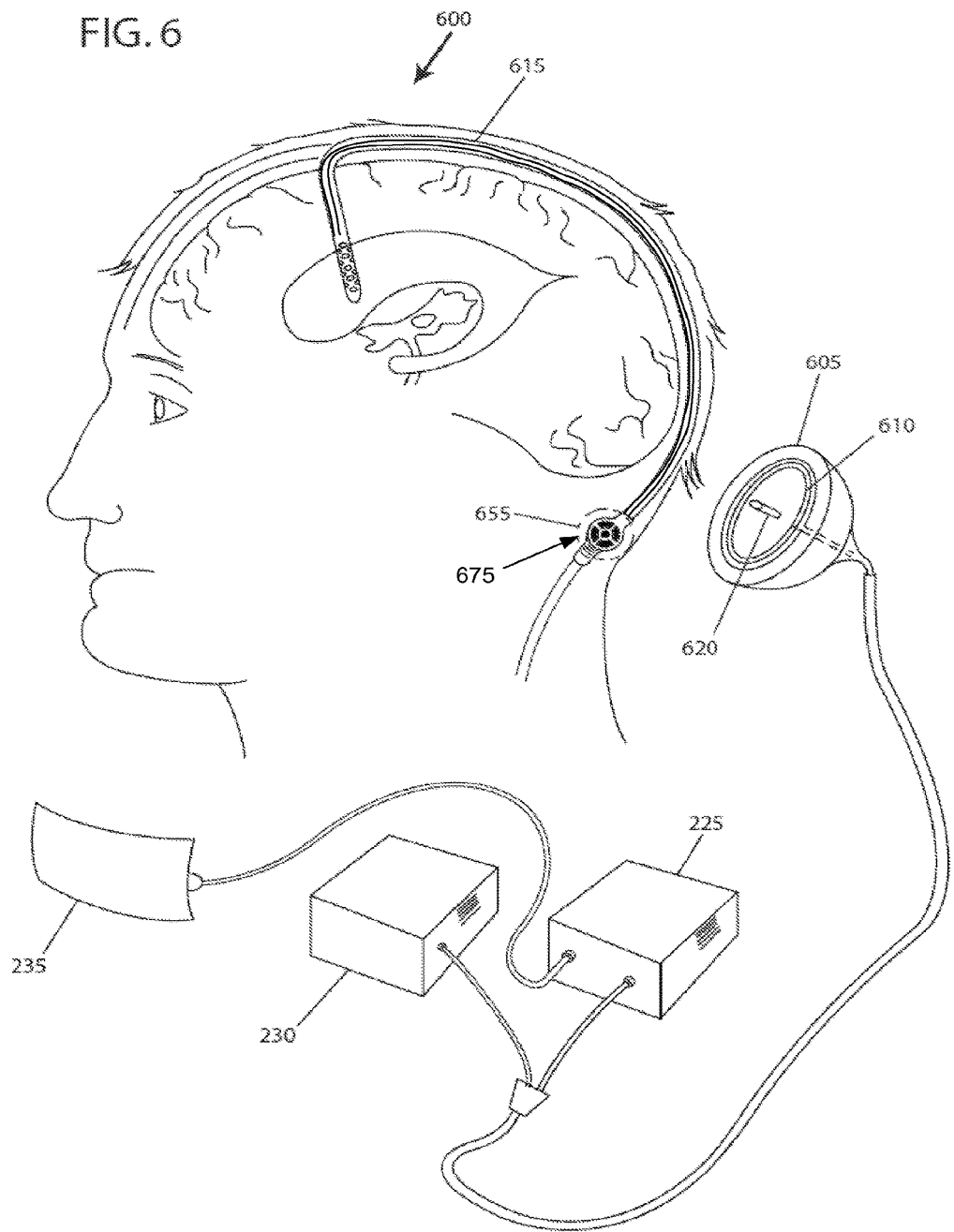

DETECTION AND CLEARING OF OCCLUSIONS IN CATHETERS

CROSS REFERENCE TO RELATED APPLICATIONS

The present application is a divisional of U.S. patent application Ser. No. 13/828,084, filed Mar. 14, 2013, the contents of which are hereby incorporated by reference in its entirety.

1. FIELD OF THE INVENTION

Examples of the present invention relates generally to catheters for removing and transporting fluid within the body, and more specifically to a catheter system with embedded wires for the detection and clearing of occlusions.

2. BACKGROUND

Brain swelling, or encephalitis, is often the result of brain injury, infection, or other malady. As the brain swells, it compresses the surrounding intracranial fluid, increasing intracranial pressure and the pressure on the brain. The condition known as congenital hydrocephalus, commonly referred to as "water on the brain," is a disorder that can result in permanently elevated intracranial pressure (ICP), requiring long-term treatment. Unfortunately, excess ICP can damage the brain physically and can reduce blood flow to the brain causing oxygen deprivation and possible death to brain tissue. This secondary type of brain injury can be more extensive than the original injury to the brain (e.g., from a head trauma).

As a result, it can be beneficial to monitor ICP for several hours or days after a head injury to ensure the brain edema subsides and to prevent further injury. In the congenital case, ICP monitoring maybe required for a lifetime. Fortunately, this overpressure situation can often be reduced, or eliminated, by simply draining a portion of the cerebral fluid out of the skull. The fluid can be drained externally, or can be transported to another part of the body for reabsorption (e.g., into the abdominal cavity).

In either case, an intracranial catheter inserted into the skull connected to a shunt can provide ICP drainage. The catheter can be completely internal or partially external to the patient's body. As shown in FIG. 1, for ICP control, for example, the catheter 105 can be implanted into the intracranial cavity (ICC) 135 through a burr hole 120 in the skull 110. For long term use, the catheter 105 can be implanted under the patient's scalp 130, for example, and drain into an internal body cavity (e.g., the abdomen) for reabsorption/removal by the body.

Because at least a portion, if not all, of the catheter 105 is implanted, detection of blockages, or occlusions, is difficult. This problem is exacerbated somewhat in the case of intracranial fluid (ICF) because ICF is also clear. This makes external detection using video imaging, for example, more difficult.

In addition, after detection, removing the occlusion using conventional techniques is difficult. One method for removal of occlusions is explanation of the catheter. In other words, the catheter is removed from the patient's body and then cleaned or replaced. This method is time consuming and requires hospital resources (e.g., operating rooms, staff, etc.). This method also represents obvious risks of infection and injury to the patient, particularly intracranial applications where brain damage is possible.

Another method is to insert a tool into the catheter to clear the blockage. This may be achieved using simple mechanical tools, such as using a balloon catheter, to dislodge and/or remove material. When using this technique, however, material removed during the process can become dislodged and travel through the patient's body only to cause a blockage elsewhere. This can result in serious complications. If this results in an arterial blockage and a loss of blood flow to the brain, for example, stroke can result.

Yet another method is the insertion of a probe into the catheter to provide some sort of electromagnetic energy to the blockage site. Radio-frequency (RF) or laser energy, for example, can excite the cells forming the blockage to the point of evaporation. This can enable the blockage to be removed, but also presents a risk of injury to the patient as the probe is manipulated to the blockage site. In addition, improper manipulation of the probe can result in unintended damage to the catheter and surrounding, healthy tissue.

What is needed, therefore, is a catheter system with built-in detection and clearing of occlusions. The catheter should provide external detection of occlusions with minimal intrusion. The catheter should also provide one or more internal means for occlusion removal without catheter explantation. The catheter should also preclude the use of external tools for occlusion removal. It is to such a system that examples of the present invention are primarily directed.

SUMMARY

Examples of the present invention relate generally to catheters for removing and transporting fluid within the body, and more specifically to a catheter system with embedded wires for the detection and clearing of occlusions. In some examples, the system can generally include a catheter with one or more drain holes, one or more wires, and a control unit. The catheter can be insertable into a patient's body and can provide drainage therefrom. The catheter can have one or more wires to enable the detection and clearing of occlusions using one or more methods.

The catheter can further include one or more sets of wires. A first set of one or more wires can be used to detect electrical changes in the catheter system circuit to detect occlusions and other problems. A second set of one or more wires can be used to transmit electromagnetic energy to the catheter to remove occlusions. In some examples, the first set and the second set of wires can be the same wires. The system can use a wired, semi-wired, or wireless probe to provide external connection to the first and second sets of wires.

Examples of the present invention can include a system with a catheter in fluid communication with a fluid of a patient's body, a shunt in fluid communication with the catheter, a detection circuit including one or more wires in electrical communication with the fluid, detecting a change in one or more electrical properties of the fluid, and a transmission circuit, with one or more other wires in electrical communication with the fluid, providing an electromagnetic signal to the fluid to remove an occlusion. In some examples, the detection circuit can include a first wire and a second wire and each wire can have one or more contacts in electrical communication with the fluid.

In some examples, the catheter can include one or more drain holes and an inner lumen. In this configuration, the one or more wires of the detection circuit can be disposed at least partially in a sidewall of the inner lumen and in electrical communication with the fluid. In some configurations, the catheter can also have a wire lumen with one or more access ports. In this manner, a portion of the one or more wires of the transmission circuit or detection circuit can be housed in the wire lumen in electrical communication with the fluid. In some examples, the system can also include an electronics interface disposed in the shunt and in electrical communication with the detection circuit, the transmission circuit, or both.

Examples of the present invention can also include a system with a catheter in fluid communication with a fluid of a patient's body, a shunt in fluid communication with the catheter, a detection circuit with one or more wires in electrical communication with the fluid, and a transmission circuit with one or more other wires in electrical communication with the fluid. The system can also have a detection unit, in electrical communication with the detection circuit, for monitoring one or more electrical properties of the detection circuit to detect an occlusion in the catheter, and an external energy source, in electrical communication with the transmission circuit for providing electromagnetic energy to the transmission circuit to remove detected occlusions.

In some examples, the external energy source can provide electromagnetic energy, such as an RF signal at a frequency between approximately 250 KHz and 2 Mhz. In other examples, the RF signal can be at a frequency of approximately 500 KHz.

Examples of the present invention can also include a system with a catheter in fluid communication with a fluid of a patient's body, a shunt in fluid communication with the catheter, a detection circuit in electrical communication with the fluid, and a transmission circuit in electrical communication with the fluid. In some examples, an electronics interface can be disposed in the shunt and in electrical communication with the detection circuit and the transmission circuit. In other examples, the system can also include a probe electrically coupleable to the electronics interface.

Examples of the present invention can also include a detection unit in electrical communication with the probe and an external energy source in electrical communication with the probe. In this configuration, the detection unit can monitor one or more electrical properties of the detection circuit to detect an occlusion when the probe is electrically coupled to the electronics interface and the external energy source can provide energy to the transmission circuit to remove detected occlusions when the probe is electrically coupled to the electronics interface. In some examples, the detection unit can detect a change in the impedance of the detection circuit. In other examples, the detection unit can detect a change in the resistance of the detection circuit.

In some examples, the system can also include a patch, disposed on the patient's skin, for example, for completing a circuit between the transmission circuit and the external energy source. In some examples, the electronics interface can have one or more sockets in electrical communication with the detection circuit, the transmission circuit, or both and the probe can have one or more pins electrically coupleable to the one or more sockets in the electronics interface.

In some examples, the electronics interface can have a first set of one or more antennas in electrical communication with the detection circuit, the transmission circuit, or both and the probe can have a second set of one or more antennas wirelessly coupleable to the first set of one or more antennas in the electronics interface. In other examples, the electronics interface can have a first antenna in electrical communication with the detection circuit and a second antenna in electrical communication with the transmission circuit. In this configuration, the probe can include a third antenna wirelessly coupleable to the first antenna and a fourth antenna wirelessly coupleable to the second antenna.

In some examples, the electronics interface can include one or more sockets in electrical communication with the transmission circuit or the detection circuit and a first set of one or more antennas in electrical communication with the other of the transmission circuit or the detection circuit. In this configuration, the probe can have one or more pins electrically coupleable to the one or more sockets in the electronics interface and a second set of one or more antennas in wirelessly coupleable to the first set of antennas. In some configurations, the electronics interface can have one or more sealed chambers and each chamber can have one or more sockets electrically coupleable to the probe. In some examples, the catheter and the shunt can be integral (i.e., made of one piece of material).

Examples of the present invention can also include a method including the steps of transmitting a first signal through a detection circuit including a detection unit and one or more wires disposed in a catheter and in electrical communication with a fluid in the catheter, detecting a change in one or more electrical properties of the detection circuit indicating an occlusion, and transmitting a second signal from an external energy source to the one or more wires disposed in the catheter to remove the occlusion. In some examples, detecting a change in the impedance of the detection circuit can indicate an occlusion. In other examples, detecting a change in the resistance of the detection circuit can indicate an occlusion.

The second signal can include, for example, an RF signal at a frequency between approximately 250 KHz and 2 MHz. In some examples, the second signal can be an RF signal at a frequency of approximately 500 KHz.

These and other objects, features and advantages of the present invention will become more apparent upon reading the following specification in conjunction with the accompanying drawing figures.

BRIEF DESCRIPTION OF THE DRAWINGS

FIG. 2 depicts a catheter system with implanted shunt and wired probe, in accordance with some examples of the present invention.

FIGS. 3a-h depict various examples of a catheter with built-in occlusion detection and removal, in accordance with some examples of the present invention.

FIG. 6 depicts a catheter system with implanted shunt and wireless probe, in accordance with some examples of the present invention.

DETAILED DESCRIPTION

Figure 1:
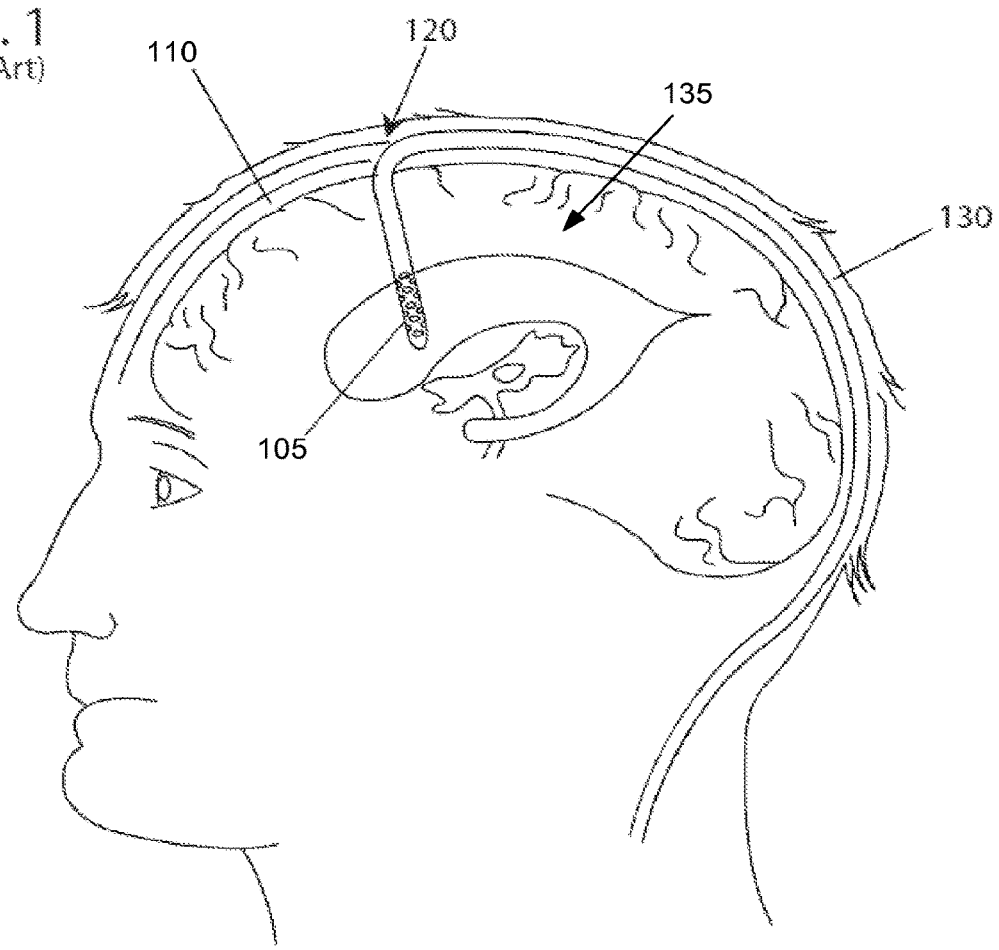
FIG. 1 depicts a convention intracranial catheter with implanted shunt.

Examples of the present invention relates generally to catheters for removing and transporting fluid within the body, and more specifically to a catheter system with included wires for the detection and clearing of occlusions. In some examples, the system can generally include a catheter with one or more drain holes, one or more wires, and a control unit. The catheter can be insertable into a patient's body and can provide drainage therefrom. The catheter can have one or more wires to enable the detection and clearing of occlusions using one or more methods.

To simplify and clarify explanation, the system is described below as a system for draining intracranial pressure (ICP) with built-in occlusion detection and removal. One skilled in the art will recognize, however, that the invention is not so limited. The system can be deployed any time a catheter is needed to add or remove fluid to or from the body or from one area of the body to another location (inside or external to the body) where access is limited and occlusions may occur. The system can be deployed, for example and not limitation, for draining urine from the bladder, drainage of urine from the kidney, the drainage of many types of fluid collections (e.g., from an abdominal abscess), or the addition of fluids and medications to specific areas.

The materials described hereinafter as making up the various elements of the present invention are intended to be illustrative and not restrictive. Many suitable materials that would perform the same or a similar function as the materials described herein are intended to be embraced within the scope of the invention. Such other materials not described herein can include, but are not limited to, materials that are developed after the time of the development of the invention, for example. Any dimensions listed in the various drawings are for illustrative purposes only and are not intended to be limiting. Other dimensions and proportions are contemplated and intended to be included within the scope of the invention.

As discussed above, a problem with conventional catheters is that occlusions are difficult to both detect and remove. Conventionally, for example, doctors have relied in X-ray, MRI, and other imaging means for the detection of occlusions. These techniques can be dangerous for patients, however, and provide only limited detection of the materials that generally include catheter blockages (e.g. dried blood or protein based occlusions). In addition, removal of these blockages requires either catheter explantation (removal) or tool insertion (e.g., a balloon catheter or a stylet type device to clear the blockage). Both of these options carry significant risk of injury, infection, and/or death to the patient.

In response, as shown in FIG. 2, examples of the present invention can include a catheter system 200 with built-in occlusion detection and removal. In some examples, the catheter system 200 can include a catheter 205 in fluid connection with an internal or external shunt 255. In some configurations, such as for the long-term drainage of intracranial fluid (ICF), the placement of the catheter 205 and shunt 255 can be subcutaneous (e.g., under the scalp 207). In this manner, the catheter 205 and shunt 255 can be unobtrusive in daily life. In addition, the installation of an extension catheter 250 can enable removal of the fluid to an acceptable internal or external location. In some examples, the extension catheter 250 can be a peritoneal catheter, for example, to enable fluid to drain into the abdominal cavity for reabsorption or removal by the body.

The catheter 205 and the shunt 255 can be in electrical communication via one or more conductors, or wires 215. As discussed below, the wires 215 can enable the external detection and removal of occlusions in the catheter 205 by the application of an electrical signal (e.g., DC or AC), radiofrequency (or RF), or other suitable signal. In some examples, therefore, the system 200 can include a measuring unit 230 and an external energy source 225.

The measuring unit 230 can utilize one or more of the wires 215 to detect a change in the electrical circuit including the catheter 205 and ICF. The measuring unit 230 can detect a change in the impedance (or resistance), for example, of the circuit to detect the presence and severity of an occlusion. In other words, the impedance of the ICF (and thus, the catheter 205) generally increases as the catheter 205 becomes occluded because the materials that form occlusions, e.g., coagulated blood, scar tissue, or other substances, generally have higher resistivity than "normal" materials such as, for example, liquid blood or chloroid plexus. In this manner, an AC signal, for example, can be applied to one or more of the wires 215 to determine the impedance of the circuit, with higher impedance indicating higher rates of occlusion. Similarly, application of a DC signal can be used to detect an increase in resistance in the circuit, which also tends to indicate an occlusion. Empirical data or mathematical or computer modeling, for example, can be used to establish a range covering newly implanted catheters to completely occluded catheters. This data can, in turn, be used to make informed treatment decisions.

As shown in FIGS. 3a-3h, the catheter 205 can include one or more drain holes 305 to enable fluid to enter a passageway, or inner lumen 310, for fluid removal from one area of the body to another. As discussed above, in some examples, the catheter 205 can be placed in the ICC and can enable ICF to enter the inner lumen 310 for removal via the catheter 205 to the abdominal cavity, or other suitable location.

In some examples, the catheter 205 and/or shunt 255 can include one or more wires 215 disposed in electrical contact with both the system 200 and the fluid in the inner lumen 310. This electrical connection can enable the external detection and removal of occlusions. In some examples, as shown in FIG. 3a-3d, a one or more wires 215 can be disposed in the sidewall 320 of the catheter such that they at least partially contact the fluid in the inner lumen 310 providing an electrical connection.

Figure 3D:
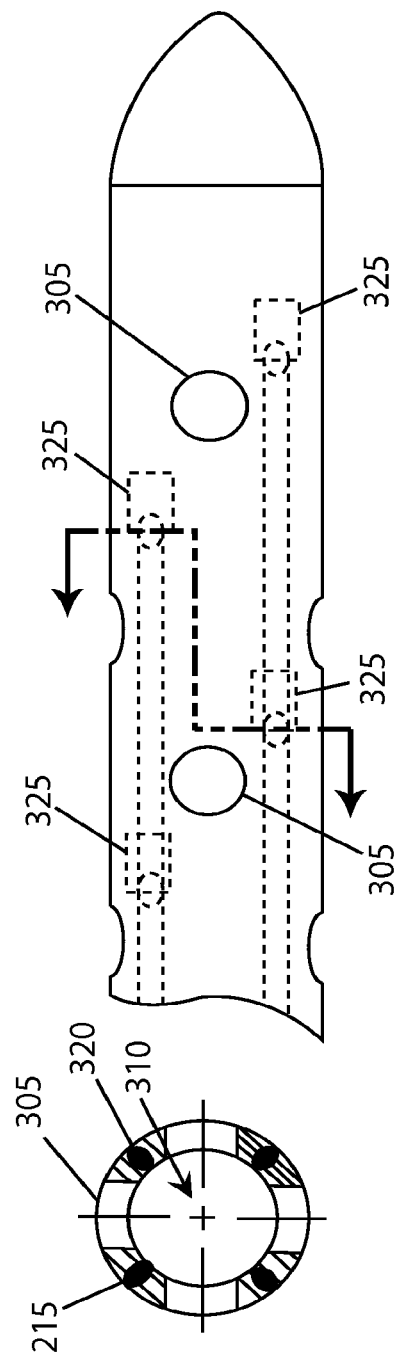
Figure 3E:
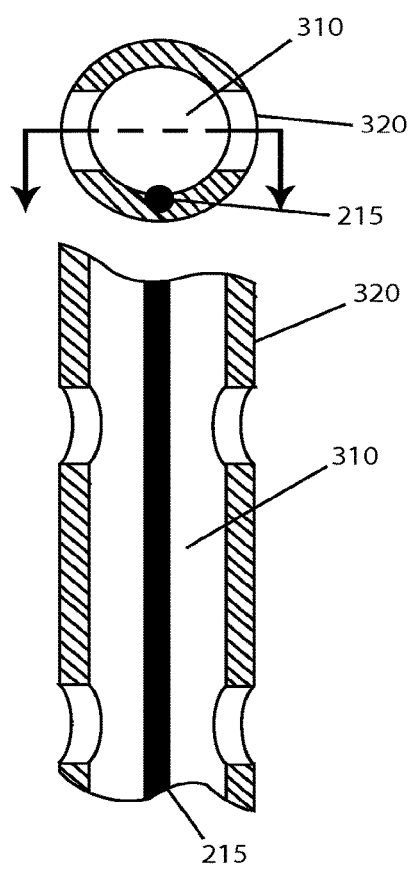
Figure 3F:
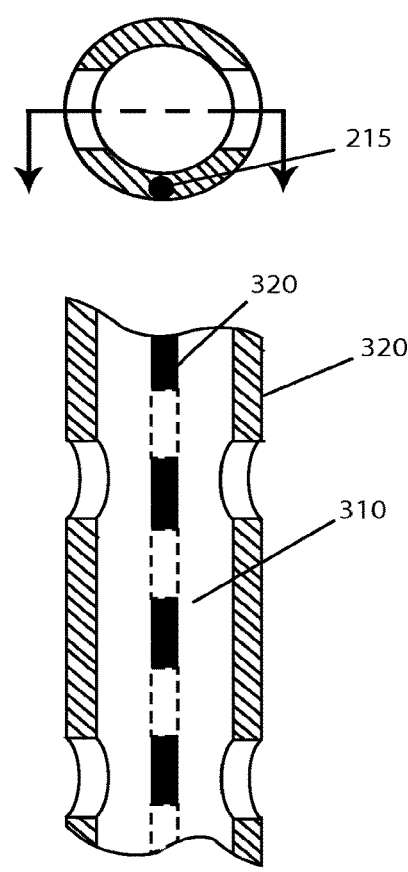
Figure 3G:
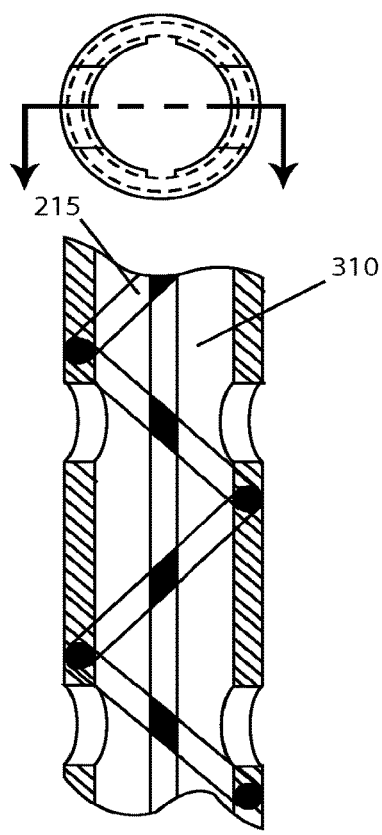
Figure 3H:
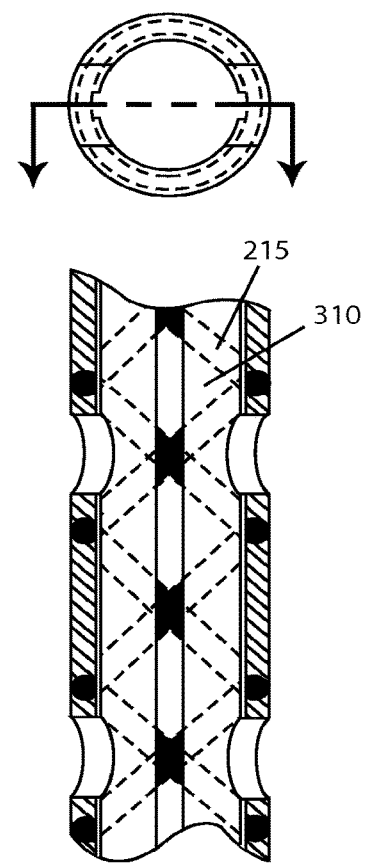

As shown, the wires 215 can be disposed such that they avoid the drain holes 305, if desired, and have one or more points of contact 325 with the fluid in the inner lumen 310. In other examples, as shown in FIG. 3e, the catheter 205 can include a single conductor 215 disposed in the sidewall 320 of the catheter 205. In this configuration, the conductor 215 can be disposed in substantially continuous contact with the fluid in the inner lumen 310. In other examples, as shown in FIG. 3f, the conductor 215 can be "stitched" into the sidewall 320 of the catheter 205, such that the conductor 215 is in regular, but not continuous, contact with the fluid in the inner lumen 310. Similarly, as shown in FIGS. 3g and 3h, the conductor 215 can be wound in a single or double helix, respectively, such that it makes regular, but not continuous, contact with the fluid in the inner lumen 310.

In some examples, electrical signals can be transmitted via the wires 215 to enable occlusion detection. In some examples, the signals can be DC signals for the measurement of resistance. In other examples, the signals can be AC signals for the measurement of impedance. In some examples, the signals can range in frequency from between approximately 100 Hz to 10 KHz. The wires 215 can be used to measure a change in the electrical behavior of the catheter 205. This can be done, for example, by monitoring the impedance (or resistance) of the catheter 205 and ICF to determine whether a blockage exists and, if so, the severity of the blockage. In this capacity, increasing the number of contact points 325 for the wires 215 with the ICF, for example, can enable more, or more precise, impedance measurements.

In some examples, the catheter 205 can include multiple contact points 325 in electrical communication with multiple wires 215. In this configuration, occlusion detection can be performed on multiple sets of wires 215 to locate the occlusion within the catheter 205. In other words, measuring the impedance of multiple pairs of contacts 325 in known locations in the catheter 205 via multiple pairs of wires 215 can enable the detection and location of the occlusion. Thus, knowing the location of the pair, or pairs, of contacts 325 with the highest impedance tends to indicate the location of the occlusion in the catheter. Of course, because additional wires 215 affect the manufacturing costs, complexity, and flexibility of the catheter 205, among other things, the precision of the measurement can be balanced against needs for a particular application.

Figure 4A:
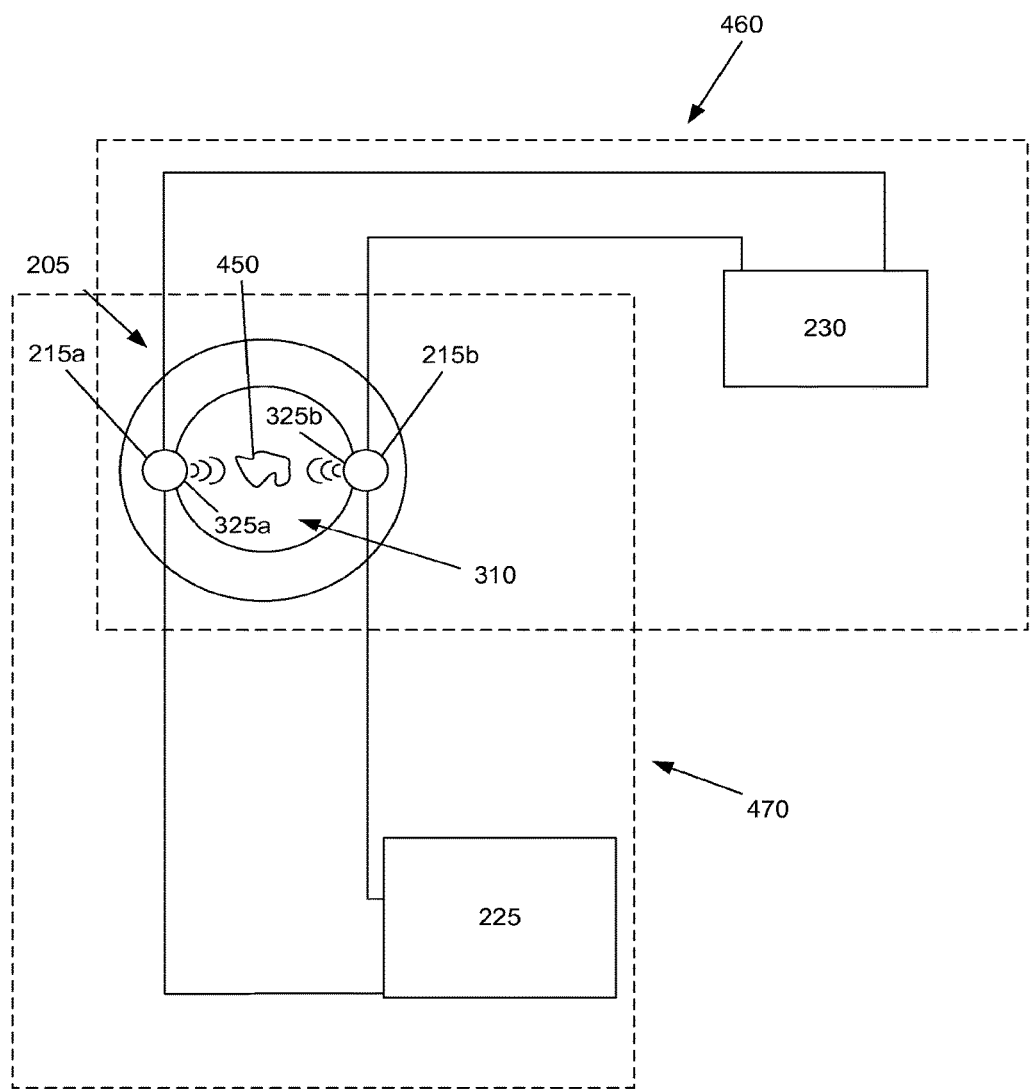
FIG. 4a is a schematic depicting the occlusion detection and removal using a bipolar system, in accordance with some examples of the present invention.

As shown in FIG. 4a, in some examples, some or all of the wires 215 can be used for both occlusion detection and removal. As shown, a detection circuit 460 can be formed between a first wire 215a and first contact 325a, the ICF and any occlusions 450 in the inner lumen 310, a second contact 325b and second wire 215b, and the detection unit 230. In this manner, a detection signal such as, for example, a DC signal can be provided by the detection unit 230 to the remainder of the detection circuit 460 to detect any changes in resistance, impedance, or other electrical properties in the circuit.

The resistance of the detection circuit, for example, can change as the organic material in the inner lumen 310 changes. A low, or baseline, resistance, for example, can indicate the presence of normal material (e.g., only ICF and/or liquid blood) in the inner lumen 310. An increase in the resistance of the detection circuit 460, on the other hand, can indicate the formation of the occlusion in the inner lumen 310 as the detection signal passes through, and is resisted by, the occlusion 450. As mentioned above, multiple wires 215, or pairs of wires 215, can be used to locate the occlusion in the catheter 205, as desired.

In other examples, the wires 215 can also be used for occlusion removal in a bipolar mode. As shown, a transmission circuit 470 can be formed between the first wire 215a and first contact 325a, the ICF and any occlusions 450 in the inner lumen 310, the second contact 325b and the second wire 215b, and the external energy source (e.g., an electromagnetic generator) 225. In this manner, the electromagnetic generator 225 can provide an energetic signal such as, for example, a high-frequency RF signal to the remainder of the transmission circuit 470. As the transmission signal passes through the occlusion 450, the RF energy excites the cells of the occlusion 450 causing them to heat and eventually vaporize. In addition, because the RF signal passes from the first wire 215a, through the occlusion 450, and returns through the second wire 215b, damage to surrounding healthy brain tissue can be minimized. In some examples, such as in a four wire catheter 205, a first pair of wires 215 can be used for detection and a second pair of wires 215 can be used for removal.

Figure 4B:
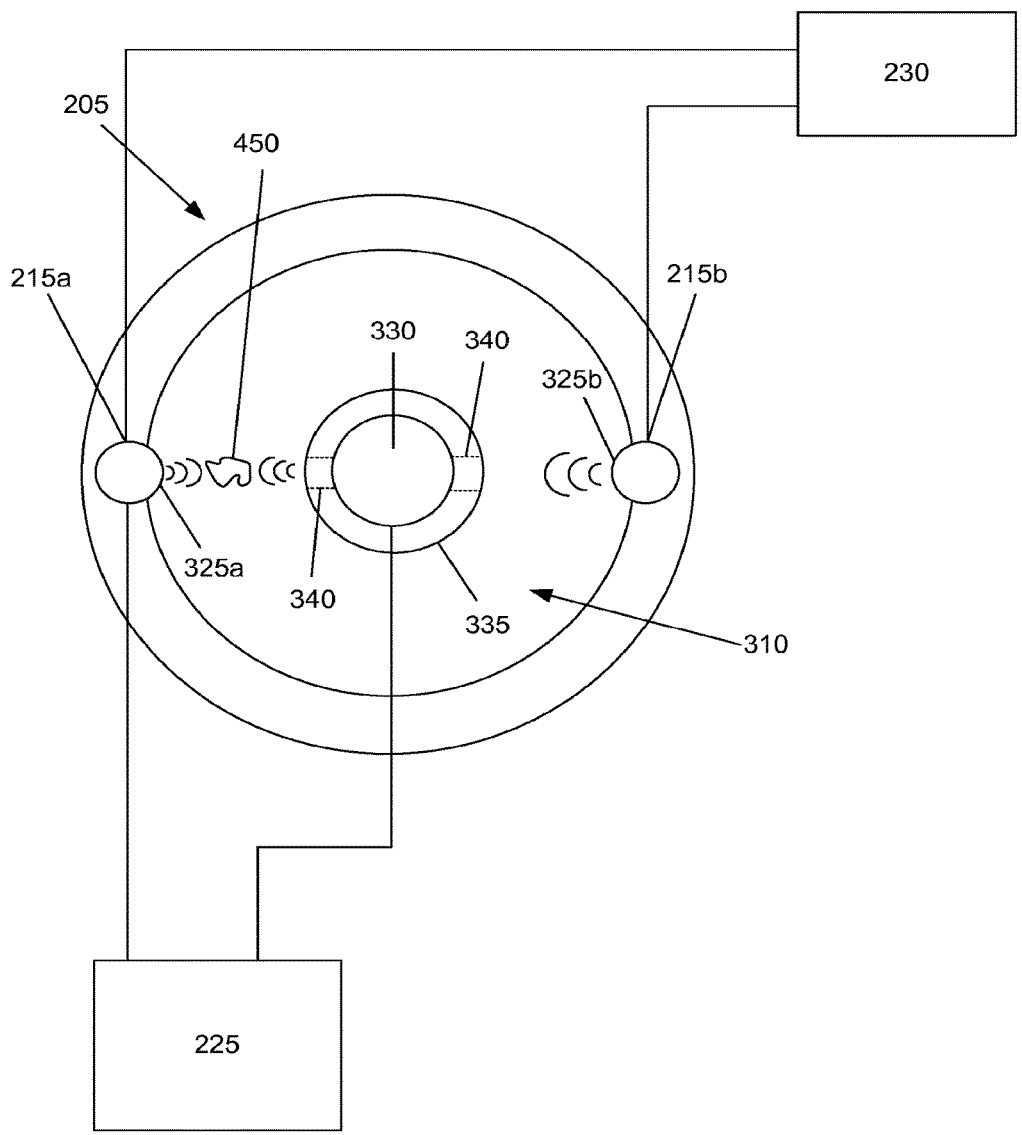
FIG. 4b is a schematic depicting the occlusion detection and removal using a bipolar system with a transmission wire, in accordance with some examples of the present invention.

As shown in FIG. 4b, in some examples, the catheter 205 can further include one or more transmission wires 330. In some examples, the transmission wire 330 can be disposed inside the inner lumen 310 and can be used to transmit detection and/or removal signals (e.g., RF) into the catheter 205. In some examples, an additional wire lumen 335 can be used to house the transmission wires 330 separately from the inner lumen 310.

In some examples, the transmission wire 330 can be in electrical contact with the fluid and/or occlusion 450 inside the inner lumen 310 via one or more ports 340. In this configuration, as before, in bipolar mode, the transmission wire 330 can form a circuit with one or more wires 215 for the detection and removal of occlusions in a manner similar to that described above. This can be useful to more specifically location an occlusion 450, for example, or when an occlusion 450 forms on one side of the inner lumen 310. In this configuration, the wires 215 and/or transmission wires 330 can be used in pairs to locate the occlusion 450 and remove the occlusion 450 in bipolar mode (i.e., any pair of wires 215, 330 can be used for either purpose or the same pair of wires 215, 330 can be used for both purposes).

Figure 4C:
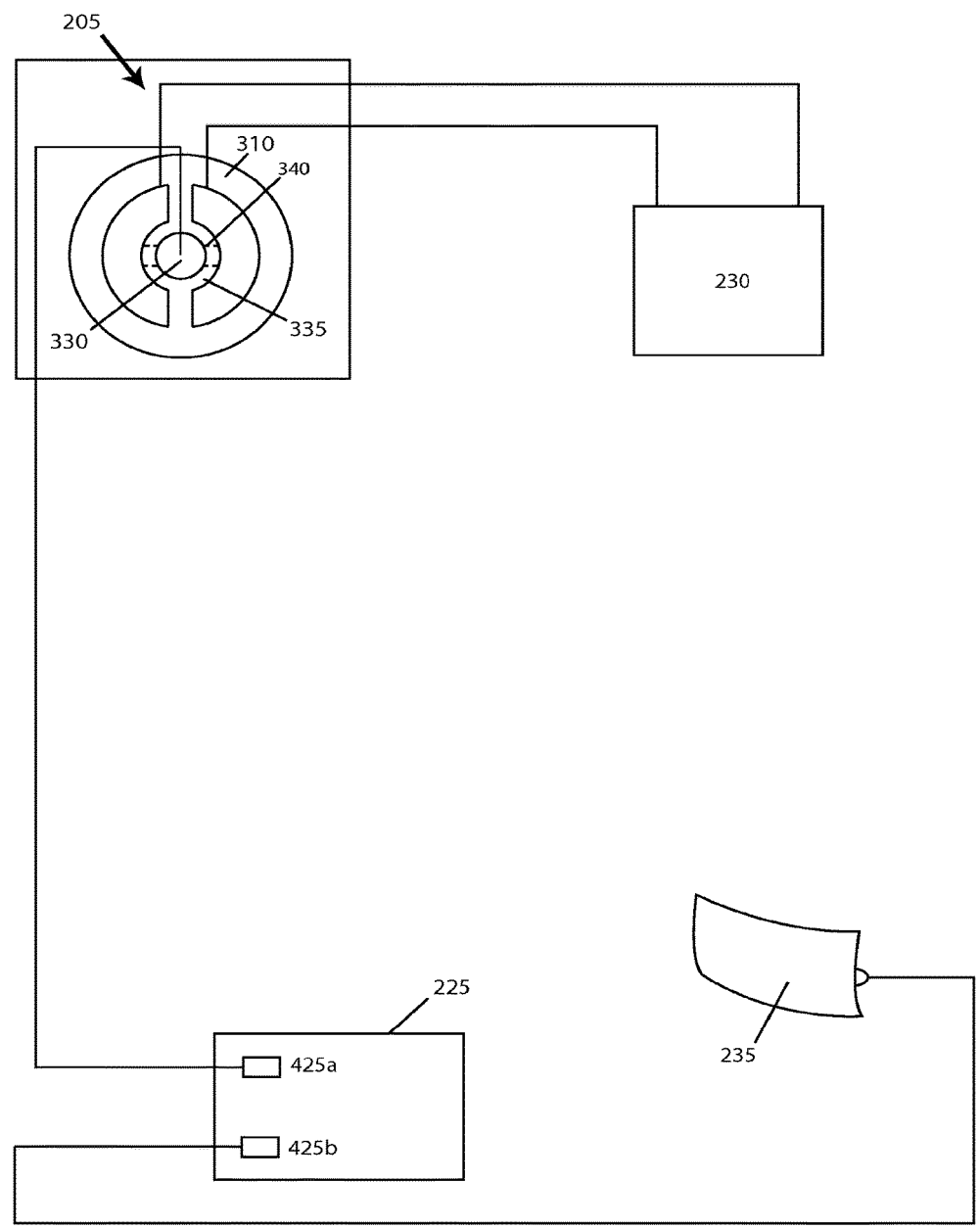
FIG. 4c is a schematic depicting the occlusion detection and removal using a monopolar system, in accordance with some examples of the present invention.

In still other examples, as shown in FIG. 4c, the transmission wire 330 can be used to provide occlusion removal in a monopolar mode. In this example, while occlusion detection can be provided using the detection unit 230 and a pair of wires 215, 330 using the bipolar method discussed above, occlusion removal can be provided by passing the transmission signal 425a through one wire 215, 330 with the signal returning 425b via a patch 235 located on, but external to the patient, to the external energy source 225. The patch 235 can be located on the patient's skin, for example, with a suitable temporary adhesive or gel. In this manner, occlusion removal can be provided using only a single wire 215, 330 in the catheter 205. This can reduce the complexity of the catheter 205 and wiring 215, 330, but requires care as the removal signal must pass through a portion of the patient's (possibly healthy) tissue to return to the patch 235 on the patient's skin. In some examples, therefore, signals with specific characteristics (e.g., frequency) can be chosen to effectively remove occlusions 450 with minimal effects on healthy tissue.

To provide a current path between the external energy source 225 and the occlusion, the wire lumen 335 can include, for example and not limitation, one or more holes, slits, or other access ports 340 to provide contact between the transmission wire 330 and fluid and/or tissue inside the inner lumen 310. The application of electromagnetic energy 425a to the any of the wires 215, 330, therefore, can travel through the wire 215, 330, through the occlusion in the catheter 205, and return 425b via another wire 215, 330 or via the return patch 235, establishing a complete circuit with the external energy source 225. The application of high-frequency RF energy, for example, can heat and evaporate the tissue causing the occlusion.

In either bipolar or monopolar mode, occlusions 450 can be cleared without removing the catheter 205. In addition, because the occlusion is within a known distance from the wires 215 and/or transmission wire 330, components of the energy source (e.g., frequency, intensity, etc.) can be chosen to maximize its effect on the occlusion 450 and minimize its effect on surrounding, healthy tissue.

As shown in FIGS. 5*a*-5*d*, in some examples, electrical contact between the wires 215, 330 inside the catheter 205 can be provided with a probe 220 and an electronic interface 275 located in the shunt 255. In some examples, as with conventional shunts, the shunt 255 can include one or more fluid valves (e.g., pressure valves) to regulate the flow of fluid. In some examples, the electronic interface 275 can be placed in the pumping chamber of the shunt 255 to provide wired or wireless connection to the wires 215, 330.

Figure 5A:
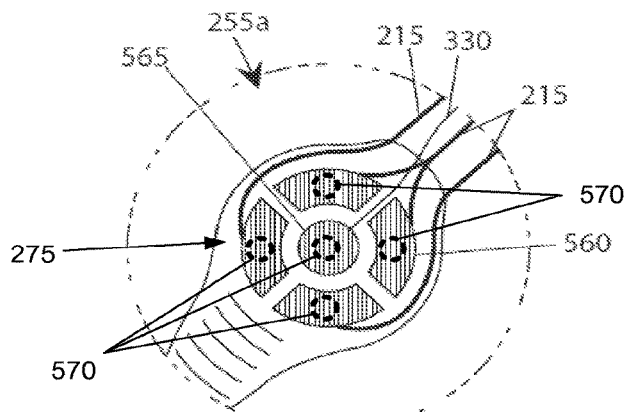
FIGS. 5a and 5c depict a five wire detection and removal system with probe, in accordance with some examples of the present invention.
Figure 5B:
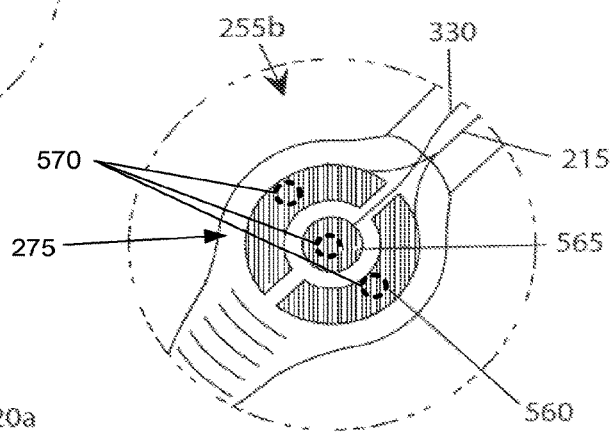
FIGS. 5b and 5d depict a three wire detection and removal system with probe, in accordance with some examples of the present invention.
Figure 5C:
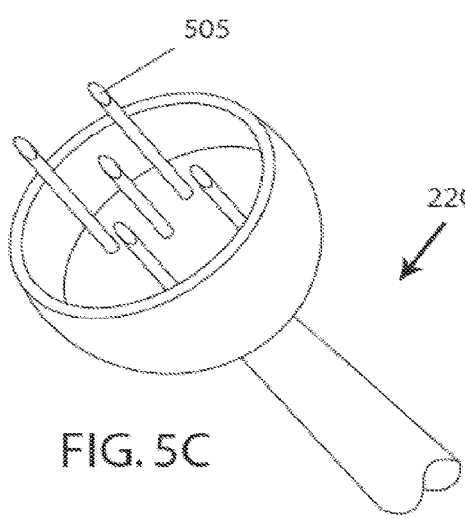
Figure 5D:
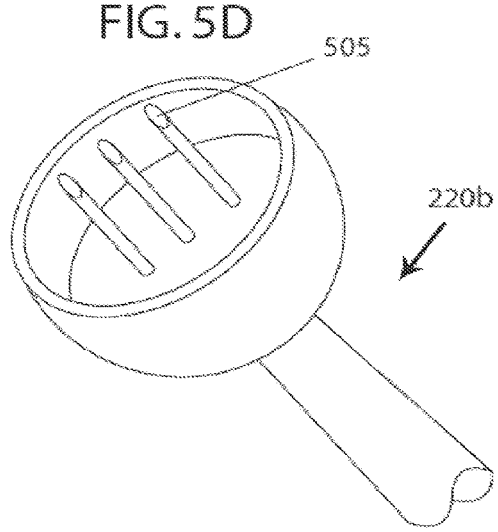

As shown, the probes 220 can have one or more pins 505 insertable into the electronic interface 275 to provide electrical contact between the wires 215, 330 and external components such as, for example and not limitation, the measuring unit 230 and electromagnetic generator 225. In some examples, as shown in FIGS. 5*a* and 5*c*, the shunt 255*a* can include four wires 215 and one transmission wire 330 with a dedicated pin 505 on the probe 220*a* for each contact. In other examples, as shown if FIGS. 5*b* and 5*d*, the shunt 255*b* can include two wires 215 one transmission wire 330, again with a dedicated pin 505 on the probe 220*b* for each contact. Of course, more or less wires 215 could be used in the system 200. So, for example, the number of wires 215 can be increased for increased sensitivity or power transmission capabilities, while fewer wires could be used to minimize cost and complexity.

In addition, as mentioned above, in bipolar mode, any of the wires 215, 330 can be used in pairs for either detection or removal of occlusions 450. Single wires 215, 330 can also be used in monopolar mode for occlusion removal, with signals returning through a patch 235 located on the patient's skin, for example.

In some examples, the electronic interface 275 can include one or more sealed chambers 560 each with an external seal 565 and an internal socket, or contact 570. In this manner, electrical contact can be made between the probe 220 and the wires 215, 330 simply by piercing the seal 565 and inserting the probe(s) 220 into the appropriate socket 270. The external seal 565 can be manufactured from latex, for example, or other suitable material to maintain the sealed chambers 560, enable probe 220 access, and to have a substantially "self-healing," or resealing, surface. In this manner, the electronic interface 275 can be accessed multiple times without significant degradation to the sealing surface 565.

For subcutaneous applications, for example, the pins 505 on the probe 220 can be sharp to minimize damage to the surrounding tissue when piercing the skin, for example. In some examples, the patient can be provided a local anesthetic and/or mild sedative to minimize discomfort. For external shunts 255, on the other hand, the electronic interface 275 can be externally accessible with the probe 220. In either configuration, the seals 565 can prevent dirt, bacteria, viruses, other pathogens, and bodily fluids, for example, from contaminating the electronic interface 275 and contacts 570. This configuration reduces both infections and other issues associated with foreign material entering the wound site and corrosion and other issues related to the conductivity of system elements (e.g., the sockets 570, or other contacts).

In some examples, one or more of the wires 215, 330 can be continuous from the electronic interface 275 in the shunt 255 to their termination point in the catheter 205. In this configuration, the catheter 205 and shunt 255 can be integral, i.e., molded, extruded, or otherwise manufactured from a single piece of material, or can be assembled prior to inserting or embedding the wires 215, 330. In other examples, one or more of the wires 215, 330 can include multiple pieces connected between the catheter 205 and the shunt 255 using suitable connectors prior to use. One skilled in the art can recognize that the wires 215, 330 can be connected using many suitable methods including, but not limited to, soldering, press-fit connectors, crimp connectors, or twist together connectors. In some examples, the connectors can both connect the wires 215, 330 and provide suitable tensile strength, electrical conductivity, and corrosion resistance for the particular application.

As shown in FIG. 6, in still other examples, the system 600 can utilize a wireless, or semi-wireless probe 605 and a wireless, or semi-wireless electronic interface 675 in the shunt 655 for connection between the system 600 (e.g., the measuring unit 230 and electromagnetic generator 225) and the wires 615. In some examples, the system can use RF, Bluetooth®, or other suitable means to provide wireless communications between the probe 605 and the electronic interface 675. In some examples, the probe 605 can include one or more antennas 610 and one or more pins 620. In this manner, the probe 605 can connect with the electronics interface 675 using fewer pins 620 (semi-wireless) or no pins 620 (wireless) than the wired examples discussed above.

In some examples, as shown, the wireless probe 605 can include an antenna 610 and a pin 620. This can enable wireless occlusion detection, for example, and monopolar occlusion clearing, as discussed above. In this configuration, clearing of occlusions can be performed using only one pin 620 and one wire 215, 330, and returning through a dermal patch 235, for example, increasing comfort to the patient. In other examples, the probe 605 can include one or more antennas 610 with no pins 620, for completely wireless detection and/or clearing of occlusions.

Figure 7A:
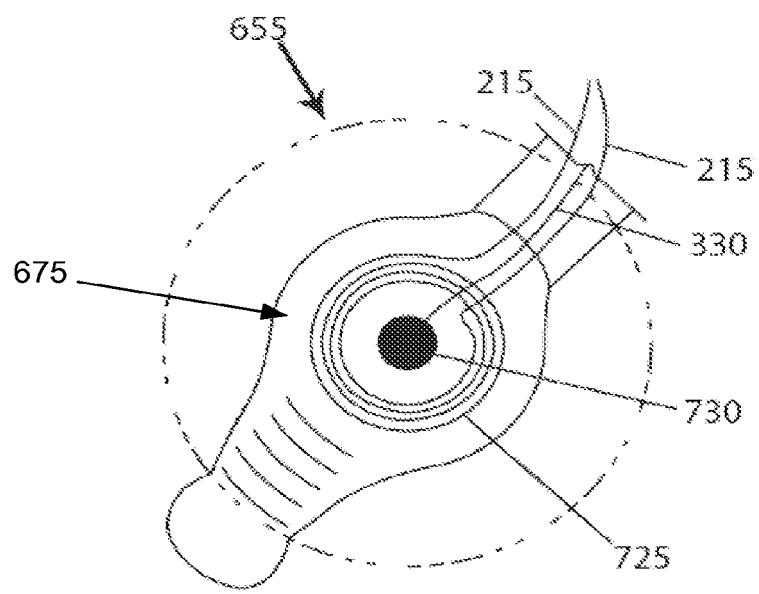
FIG. 7a depicts an electronics interface with wired and wireless connections, in accordance with some examples of the present invention.

As shown in FIG. 7*a*, in some examples, the electronic interface 675 in the shunt 655 can include one or more antennas 725 to provide wireless communication with the antenna 610 of the wireless probe 605. In some examples, the electronic interface 675 can further include one or more sockets 730 to provide wired communication with the one or more pins 620 in the wireless probe 605. In this configuration, the wireless probe 605 can be in both wired and wireless communication (i.e., semi-wireless) with one or more of the wires 215, 330 in the electronics interface 675. As a result, the antenna 610 can be used for the detection of occlusions, for example, while the pin(s) 620 can be used to transmit energy via the transmission wire 330 to remove occlusions, or vice-versa. Of course, other configurations are possible and are contemplated herein.

Figure 7B:
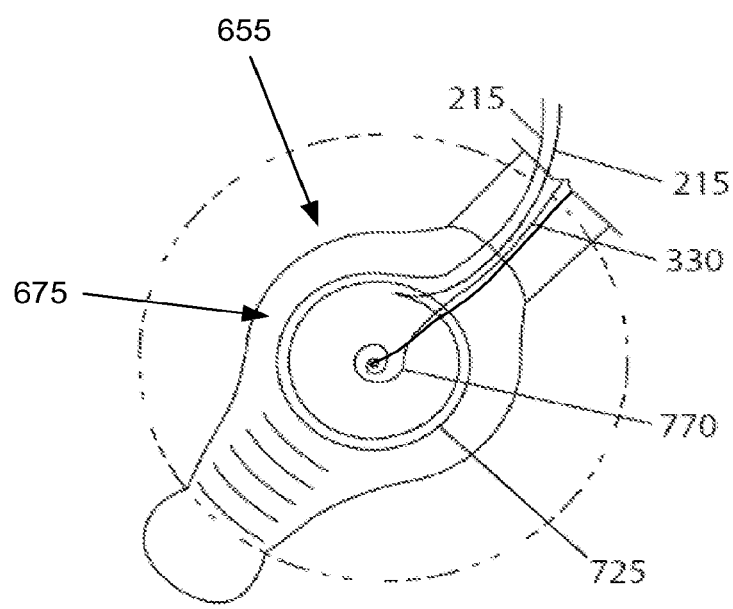
FIG. 7b depicts an electronics interface with only wireless connections, in accordance with some examples of the present invention.
Figure 8A:
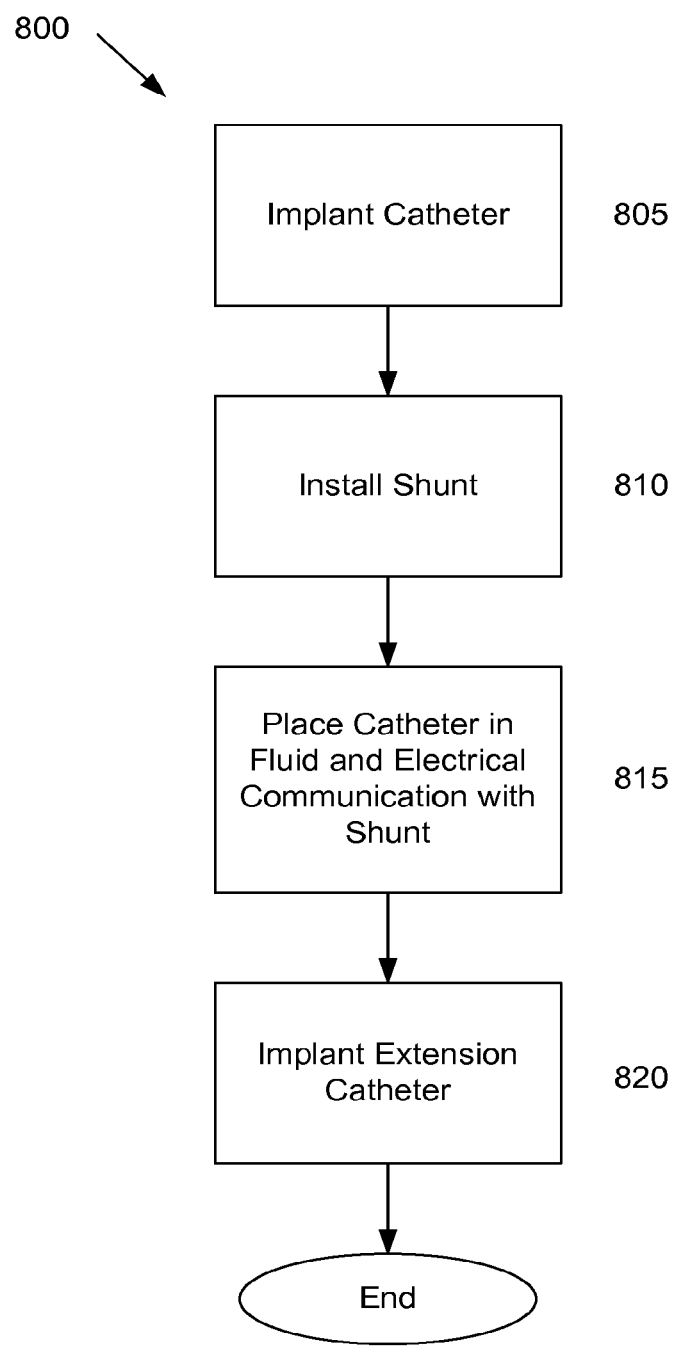
FIG. 8a is a flowchart depicting a method for implanting a catheter with integral occlusion detection and removal, in accordance with some examples of the present invention.
Figure 8B:
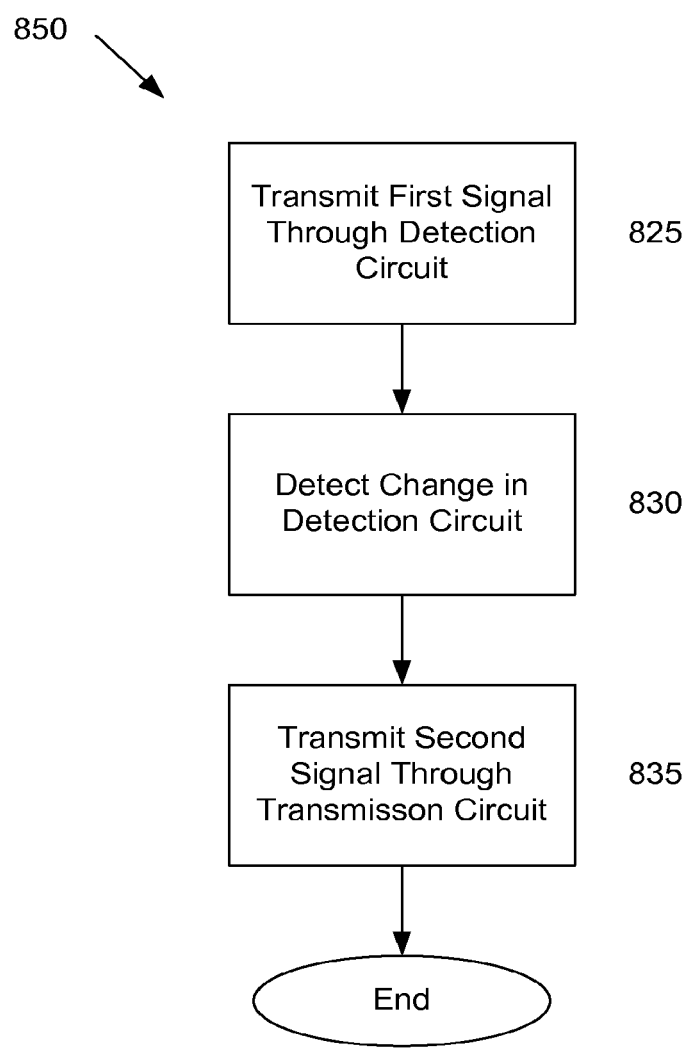
FIG. 8b is a flowchart depicting a method for occlusion detection and removal, in accordance with some examples of the present invention.

In other examples, as shown in FIG. 7*b*, the wireless probe 605 can communicate with the electronic interface 675 in the shunt 655 completely wirelessly obviating the need for the one or more pins 620. In this configuration, the wireless probe 605 can include one or more antennas 610 and the electronic interface 675 can include one or more antennas 725, 770 in electrical communication with the wires 215, 330. In this configuration, one antenna 725 can be in communication with the one or more detection wires 215 and another antenna 770 can be in communication with the one or more transmission wires 330 (or vice-versa) to provide completely wireless functionality. Of course, more or less antennas 725, 770 could be used, for example, to provide wireless connectivity to multiple pairs of wires 215, 330 for occlusion location detection, as discussed above, or for additional functionality.

Examples of the present invention can also include a method 800 for installing a catheter and/or shunt with occlusion detection and removal. In some examples, the method can include installing, or implanting, a catheter into a suitable location 805. As discussed above, in some examples, this location can be in the ICC for monitoring ICP and removing ICF, as necessary. In other examples, the catheter can be implanted into a renal passage for urinary evacuation or placed abdominally for fluid removal. Of course, catheters can be implanted in many locations in the body for which fluid evacuation or delivery are needed.

In some examples, the catheter can be installed completely internally. An intracranial catheter, for example, can be installed in the ICC and then routed outside the skull, but under the scalp. In other examples, the catheter can be placed in an appropriate internal location, but then exit the body through an access hole. This can be useful when evacuating waste to a colostomy bag, for example, or monitoring blood loss.

In some examples, the method 800 can also include installing, or implanting, a shunt 810 with an electronics interface and/or one or more fluid valves. Depending on the catheter installation, the shunt can be installed internally (implanted) or externally. In some examples, the shunt can be installed under the skin. In this manner the shunt is relatively unobtrusive visually, but can still be accessed. In other examples, such as when an external catheter is used, the shunt may be simply attached to the end of the catheter body.

In some examples, the shunt can be placed in fluid and/or electrical communication with the catheter 815. As described above, the shunt can include one or more contacts in electrical communication with the wires in the catheter. In some examples, the shunt and the catheter can be integrally manufactured with the wires running continuously throughout. In other examples, the catheter and the shunt can include connectors for placing the shunt and catheter in electrical communication. In some examples, the shunt can also include a fluid control valve, pressure valve, or other means of fluid control for the fluid in the catheter.

In some examples, the shunt can also be placed in fluid communication with an extension catheter 820. The extension catheter can enable removal of the fluid from the main catheter to a suitable location. For internal installations, such as long term ICP control, the shunt can be placed in fluid communication with a peritoneal catheter, for example, to enable fluids to be removed from the ICC to the abdomen for removal or reabsorption by the body. In other examples, the extension catheter can be external and can be in fluid communication with a collection means, such as a bag.

Examples of the present invention can also include a method of detecting and clearing occlusions in the catheter 850. In some examples, the method can include transmitting a first signal through the detection circuit 825. In some examples, the first signal can be, for example and not limitation, a DC signal, an AC signal, or an RF signal. In a bipolar method, the first signal can be transmitted through one or more pairs of wires such that the fluid in the catheter forms a part of the circuit. In this manner, changes in the detection circuit can indicate an occlusion, or other issues, inside the catheter.

The method can also include detecting a change in the first signal 830, indicting a change in the detection circuit. Using a DC signal for the first signal, for example, can enable the detection of a change in the resistance of the detection circuit, possibly indicating an occlusion. In other examples, the first signal can be an AC signal for detecting the impedance of the detection circuit, possibly indicating an occlusion. In still other examples, the first signal can be an RF signal and an occlusion may be detected by a change in the frequency, amplitude, or other property of the signal.

In some examples, the method can also include transmitting a second signal through one or more of the wires to remove the occlusion 835. The second signal can include a high-frequency RF signal, for example, that can excite and heat the material forming the occlusion to the point of vaporization. In other examples, the second signal can include other types of waves to evaporate, disrupt, or dislodge the occlusion. The second signal can be transmitted and return via one or more pairs of wires in a bipolar system; or, the second signal can be transmitted via one or more wires and return via a dermal patch, or similar, in a monopolar system.

The system 200, 600 disclosed above can provided wired, semi-wireless, or wireless detection and removal of occlusions in a number of artificial vessels including, but not limited to, catheters, stents, and tubes. The system 200, 600 can use a variety of electromagnetic energy such as, for example, DC, AC, or RF to detect partial or complete occlusions of the vessel. The system 200, 600 can also use high-energy electromagnetic energy to vaporize, pulverize, or otherwise remove occlusions in situ. In this manner, the occlusion can be removed without removing the catheter, for example, reducing a number of risks to both patients and doctors.

The system 200, 600 can include a plurality of wires 215, 330, which can be used in pairs in a bipolar system for the detection and removal of occlusions. The wires 215, 330 can also be used in a monopolar system for occlusion removal, in which a wire 215, 330 carries a transmission signal and a patch 235 on the patient's skin returns it. The system 215, 330 can include multiple wires 215, 330 with multiple contact points 325 in the catheter 205 to enable accurate occlusion location.

While several possible examples are disclosed above, examples of the present invention are not so limited. For instance, while catheters and stents have been disclosed, other medical tubes or vessels could be equipped with the system 200, 600 without departing from the spirit of the invention. In addition, the location and configuration used for the measuring unit, electromagnetic generator, electronics interface, and other components can be varied based on patient physiology, the placement of the catheter, and/or the mounting location on the patient. Modifications can be made to account for, for example, the materials used and/or space or power constraints. Such changes are intended to be embraced within the scope of the invention.

The specific configurations, choice of materials, and the size and shape of various elements can be varied according to particular design specifications or constraints requiring a device, system, or method constructed according to the principles of the invention. Such changes are intended to be embraced within the scope of the invention. The presently disclosed examples, therefore, are considered in all respects to be illustrative and not restrictive. The scope of the invention is indicated by the appended claims, rather than the foregoing description, and all changes that come within the meaning and range of equivalents thereof are intended to be embraced therein.

What is claimed is:

1. A system comprising:
a catheter in fluid communication with a fluid of a patient's body;
a shunt in fluid communication with the catheter;
a detection circuit comprising one or more wires in electrical communication with the fluid, detecting a change in one or more electrical properties of the fluid to detect an occlusion in the catheter; and
a transmission circuit, comprising one or more other wires in electrical communication with the fluid, providing an electromagnetic signal to the fluid to remove the occlusion in the catheter; wherein:
the catheter comprises one or more drain holes and an inner lumen;
the one or more wires of the detection circuit, the transmission circuit, or both are disposed at least partially in a sidewall of the catheter and in electrical communication with the fluid;
the catheter further comprises a wire lumen with one or more access ports; and
a portion of the one or more wires of the transmission circuit, detection circuit, or both are housed in the wire lumen in electrical communication with the fluid.

2. The system of claim 1, wherein the detection circuit comprises a first wire and a second wire; and
wherein each wire comprises one or more contacts in electrical communication with the fluid.

3. The system of claim 1, further comprising:
an electronics interface disposed in the shunt and in electrical communication with the detection circuit, the transmission circuit, or both.

4. The system of claim 1, further comprising:
an external energy source, in electrical communication with the transmission circuit, providing the electromagnetic signal to the fluid to remove the occlusion in the catheter.

5. The system of claim 4, wherein the external energy source provides a radio-frequency (RF) signal at a frequency between approximately 250 KHz and 2 Mhz.

6. The system of claim 5, wherein the external energy source provides an RF signal at a frequency of approximately 500 KHz.

7. A method of using the system of claim 1, the method comprising:
transmitting a first signal through the detection circuit;
detecting a change in one or more electrical properties of the detection circuit indicating an occlusion in the catheter; and
transmitting a second signal through the transmission circuit to remove the occlusion.

8. The method of claim 7, wherein detecting a change in the impedance of the detection circuit indicates an occlusion.

9. The method of claim 7, wherein detecting a change in the resistance of the detection circuit indicates an occlusion.

10. The method of claim 7, wherein the second signal comprises an RF signal at a frequency between approximately 250 KHz and 2 MHz.

11. The method of claim 10, wherein the second signal comprises an RF signal at a frequency of approximately 500 KHz.

* * * * *